United States Patent [19]

Sakamaki et al.

[11] Patent Number: 5,364,558
[45] Date of Patent: Nov. 15, 1994

[54] ESTER DERIVATIVES

[75] Inventors: Yumiko Sakamaki, Saitama; Tomijiro Naito, Tokyo; Toshiro Yukinari, Yamanashi, all of Japan

[73] Assignee: Citizen Watch Co., Ltd., Tokyo, Japan

[21] Appl. No.: 94,569

[22] Filed: Jul. 20, 1993

[30] Foreign Application Priority Data

Jul. 20, 1992 [JP] Japan .................................. 4-214536

[51] Int. Cl.$^5$ ...................... C09K 19/52; C07C 69/76
[52] U.S. Cl. ................................ 252/299.01; 560/8
[58] Field of Search ........... 252/299.01, 299.6, 299.61, 252/299.63, 299.64, 299.65, 299.66, 299.67; 560/8

[56] References Cited

FOREIGN PATENT DOCUMENTS

| | | |
|---|---|---|
| 0008061 | 7/1979 | European Pat. Off. . |
| 0203195 | 10/1985 | European Pat. Off. . |
| 5117206 | 5/1993 | Japan . |
| 5125019 | 5/1993 | Japan . |
| 2070593 | 1/1981 | United Kingdom . |

OTHER PUBLICATIONS

Week 8726, Derwent Publications Ltd., AN 87-183179 & JP-A-62 114 927, 26 May 1987.
Journal of the Indian Chemical Society, vol. 40, No. 10, 1963, pp. 851-856.
Chemical Abstracts, vol. 84, 1976, abstract no. 160598p, p. 117.
Journal of the Chemical Society, Part B, 1971, pp. 1818-1819.
Chemical Abstracts, vol. 95, 1981, abstract no. 131911g, p. 588.
Chemical Abstracts, vol. 103, 1985, abstract no. 53431t, p. 522.
Chemical Abstracts, vol. 98, 1983, abstract no. 178451j, p. 576.
CA:108(3):2/502d.
CA:92(15):128177e.
CA:75(17):109534b.

*Primary Examiner*—Shean Wu
*Attorney, Agent, or Firm*—Flynn, Thiel, Boutell & Tanis

[57] ABSTRACT

An ester derivative represented by the following formula (I).

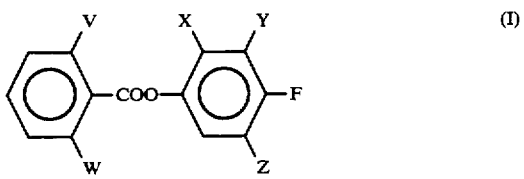

In the formula, V, W, X, Y and Z represent a hydrogen atom or a halogen atom, respectively. The present invention also comprises a liquid crystal composition containing the ester derivative. The ester derivative can optimize the n value, lower the viscosity and reduce the threshold voltage Vth of the liquid crystal composition.

11 Claims, 5 Drawing Sheets

ESTER DERIVATIVES

BACKGROUND OF THE INVENTION

This invention relates to an ester derivative useful as a liquid crystal material and a liquid crystal composition containing the ester derivative.

Liquid crystal displays are widely utilized for watches, electronic calculators, word processors, televisions and the like. Among various liquid crystal displays, a common one is the liquid crystal display in TN type (twisted nematic type) which utilizes optical anisotropy and dielectric anisotropy of a liquid crystal material.

The liquid crystal materials which are presently used for liquid crystal displays, such as a TN type, are required to have a wide liquid crystal temperature range, a rapid electro-optical response, a wide visual angle range, a low driving electric voltage, a chemical stability, an optical stability, and the like.

In order to obtain a wide visual angle range and a high contrast, it is necessary to optimize the retardation of the liquid crystal layer, i.e. $\Delta n \cdot d$ ($\Delta n$ : birefringence of liquid crystal material, d: thickness of liquid crystal layer). In the liquid crystal displays to be put to practical use, the thickness of the liquid crystal layer is set in a restricted range, and accordingly, the optimization of $\Delta n$ of the liquid crystal material is necessary.

The liquid crystal material is also desired to have a low viscosity for speeding up of the response. The relation between the rise time $\tau$ on at the time of impressing electric voltage and the decay time $\tau$ off at the time of breaking electric voltage is represented by the following formulas:

$$\tau\ on = \eta_{ii} d^2 (\epsilon_0 \Delta \epsilon V^2 - K\pi^2)^{-1}$$

$$\tau\ off = \eta_{ii} d^2 / \pi^2 K$$

In the formulas, $\eta_{ii}$ is a parameter of viscosity, d is the thickness of the liquid crystal layer, $\epsilon_0$ is the dielectric constant in vacuum, $\Delta \epsilon$ is the anisotropy of the dielectric constant, V is the impressed electric voltage, $K = K_{11} + (K_{33} - 2K_{22})/4$ ($K_{11}$: spraying elastic modulus, $K_{22}$: twisting elastic modulus, $K_{33}$: bending elastic modulus). Accordingly, in order to raise the response speed, it is essential that the liquid crystal material has a low viscosity, i.e. a low viscosity liquid crystal compound is essential.

Moreover, the driving electric voltage depends upon the threshold voltage Vth, and a liquid crystal display can be driven by a lower electric voltage by reducing the threshold voltage Vth. Accordingly, a liquid crystal material capable of reducing the threshold electric voltage Vth is required.

There has not been found a liquid crystal compound which satisfies all of the above required properties in a single material. Accordingly, in order to comply with the requirement, several kinds of liquid crystal compounds having various properties were mixed with a non-liquid crystal compound and put to practical use.

SUMMARY OF THE INVENTION

An object of the invention is to provide an ester derivative capable of optimizing the $\Delta n$ value, lowering the viscosity and reducing the threshold voltage Vth of a liquid crystal composition after being blended therewith.

The present invention provides an ester derivative which has achieved the above object, which is represented by the following formula (I):

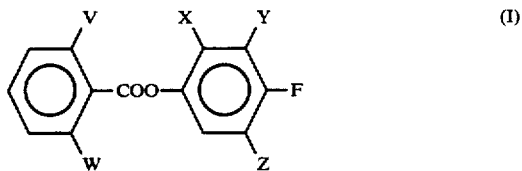

In the formula, V,W,X,Y and Z represent a hydrogen atom or a halogen atom, respectively.

DETAILED DESCRIPTION OF THE INVENTION

The halogen atom includes fluorine, chlorine and bromine, and fluorine is preferred. Preferable ester derivatives are those of Examples 1, 2, 3, 5, 6, 7, 9 described later, and those of Examples 1, 2 and 6 are particularly preferred. Two or more of the ester derivatives may be combined.

The ester derivative of the invention can be prepared according to various known esterification methods, and a typical method is to react a halogenated benzoyl halide with a halogenated phenol. The halogenated benzoyl halide can be prepared from a halogenated benzoic acid by reacting with a halogenating agent, such as thionyl chloride and phosphorus pentoxide. Then, the halogenated benzoyl halide is reacted with a halogenated phenol to produce the object ester derivative.

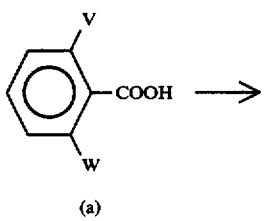

(a)

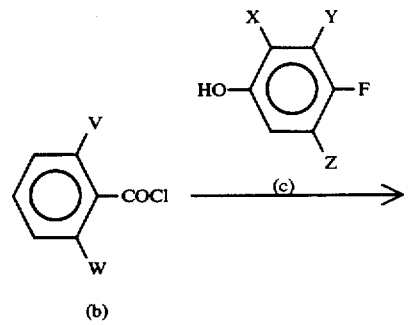

(b)

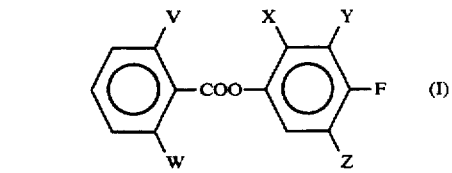

(I)

Purification of the ester derivative from the reaction mixture may be conducted by a common method, such as recrystallization, fractional distillation and washing with water.

The ester derivative does not exhibit liquid crystal properties by itself. It is blended with liquid crystal compound(s) to form a liquid crystal composition. As the liquid crystal compound blendable with the ester derivative of the invention, there are various ester compounds, cyclohexyl phenyl compounds, biphenyl compounds, pyrimidine compounds, dioxane compounds, tolan (diphenylacetylene) compounds, and the like capable of exhibiting liquid crystalizability. Preferable liquid crystal compounds are ester compounds and cyclohexylphenyl compounds, and include 4-alkylcyclohexane carboxylic acid-(4-cyanophenyl) ester, 4-alkylcyclohexane carboxylic acid-(4-alkoxyphenyl) ester, 4-alkyl-(4-cyanophenyl) cyclohexane and the like.

The liquid crystal composition consists essentially of the ester derivative and a liquid crystal compound, and may contain a chiral material as a third component.

A suitable blending amount of the ester derivative in the liquid crystal composition is 0.1 to 20 wt. %, preferably 3 to 10 wt. %, particularly preferably 4 to 8 wt. The content of the third component is less than 3 wt. %, usually less than 1 wt. %.

The blending is conducted according to a known method, such as mixing with heating to obtain a liquid state.

The ester derivative of the invention can optimize Δn, can lower threshold voltage Vth and can reduce viscosity of a liquid crystal composition by being blended therewith. Thereupon, the liquid crystal composition containing the ester derivative of the invention has excellent properties as a liquid crystal material, and liquid crystal displays loaded with the liquid crystal composition have good displaying properties. Futhermore, the ester derivative of the invention has a great mutual solubility with various compounds, and can be combined as a constituent of a liquid crystal composition with many liquid crystal materials to improve the properties of the liquid crystal composition.

EXAMPLES

EXAMPLE 1

Figure 1:
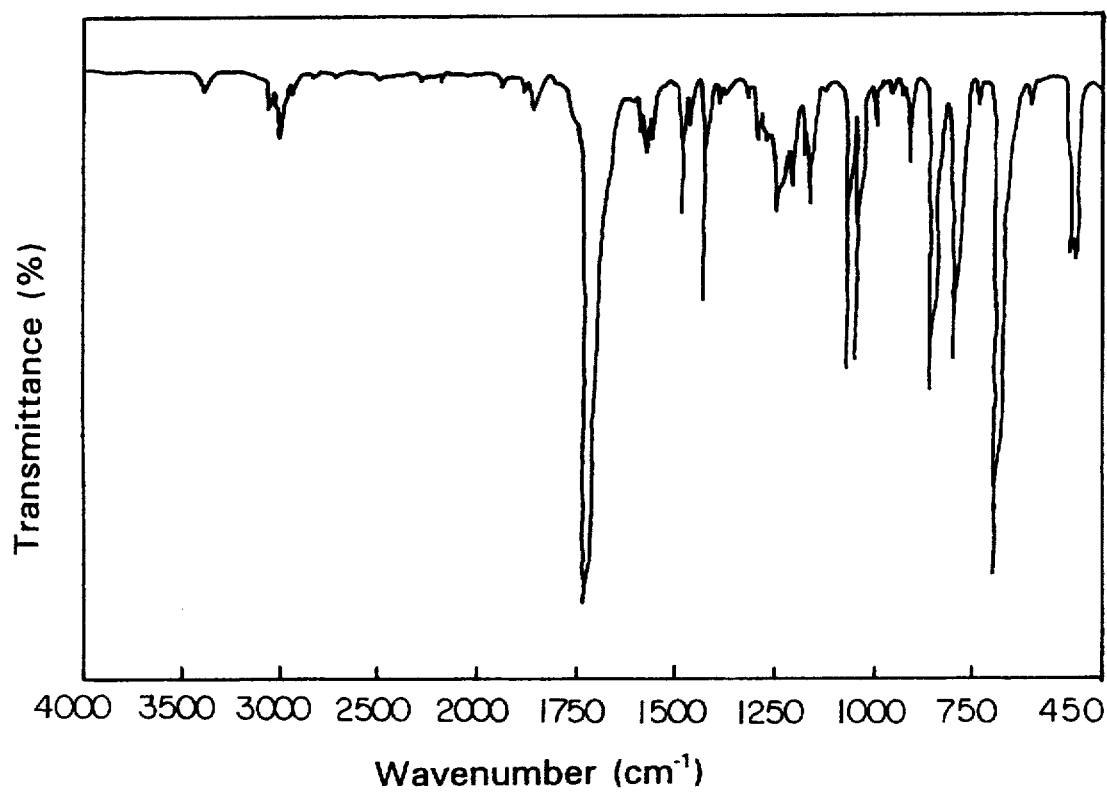
FIGS. 1 through 9 are graphs illustrating infrared spectra of examples of the ester derivative of the invention.

To 12.2 g of benzoic acid, 24 g of thionyl chloride was added, and allowed to react under reflux for 2 hours. Alter the termination of the reaction, thionyl chloride was evaporated under reduced pressure, and then distilled under reduced pressure at 20 mmHg to obtain 10 g of benzoic acid chloride at a distillation temparature of 105° C. The benzoic acid chloride was dissolved in 50 ml of toluene, ant added with 8 g of 4-fluorophenol and 8 g of pyridine to react at 40 ° C. for 3 hours. After the termiration of the reaction, 100 ml of water was added, and the organic layer was separated. The organic layer was washed with dilute hydrochloric acid, dilute alkali aqueous solution and saturated sodium chloride solution successively, and then, dried by adding anhydrous sodium sulfate. Subsequently, the organic layer was filtered, and solvent was evaporated from the filtrate under reduced pressure. The reaction product was recrystallized from hexane, and then distilled under reduced pressure at 1 mmHg to collect the fractions at a distillation temperature of 160° C. Thus, 9 g of benzoic acid (4-fluorophenyl) ester represented by the following formula was obtained. The melting point of the ester was 58.0° C. The infrared absorption spectrum of the ester is shown in FIG. 1.

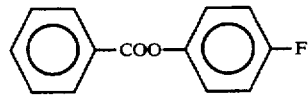

EXAMPLE 2

10 g of 2-fluorobenzoic acid-(4-fluorophenyl) ester represented by the following formula was prepared similar to Example 1, except that 14.6 g of 2-fluorobenzoic acid was used instead of 12.2 g of benzoic acid.

Figure 2:
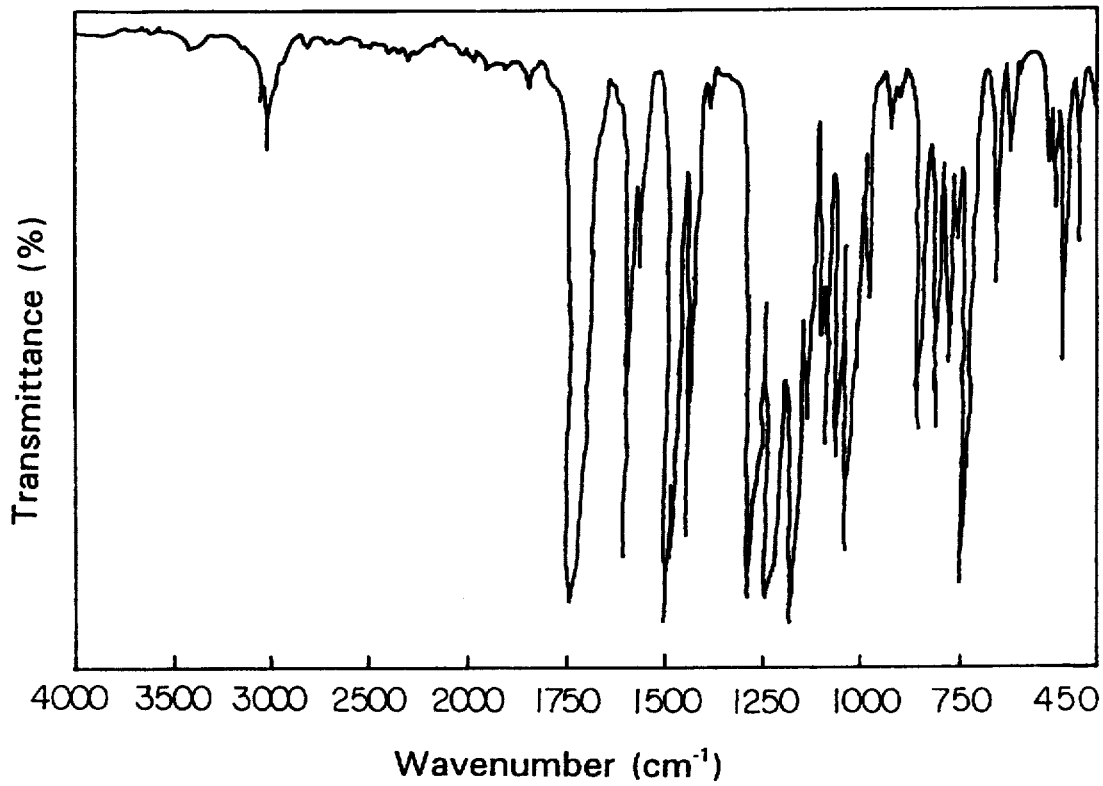

The ester had a melting point of 40.8° C., a boiling point of 150° C. at 1 mmHg and an infrared absorption sprectrum as shown in FIG. 2.

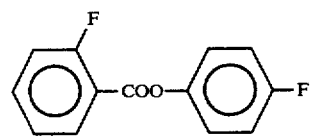

EXAMPLE 3

11 g of 2,6-difluorobenzoic acid-(4-fluorophenyl) ester represented by the following formula was prepared similar to Example 1, except that 16.2 g of 2,6-difluorobenzoic acid was used instead of 12.2 g of benzoic acid.

Figure 3:
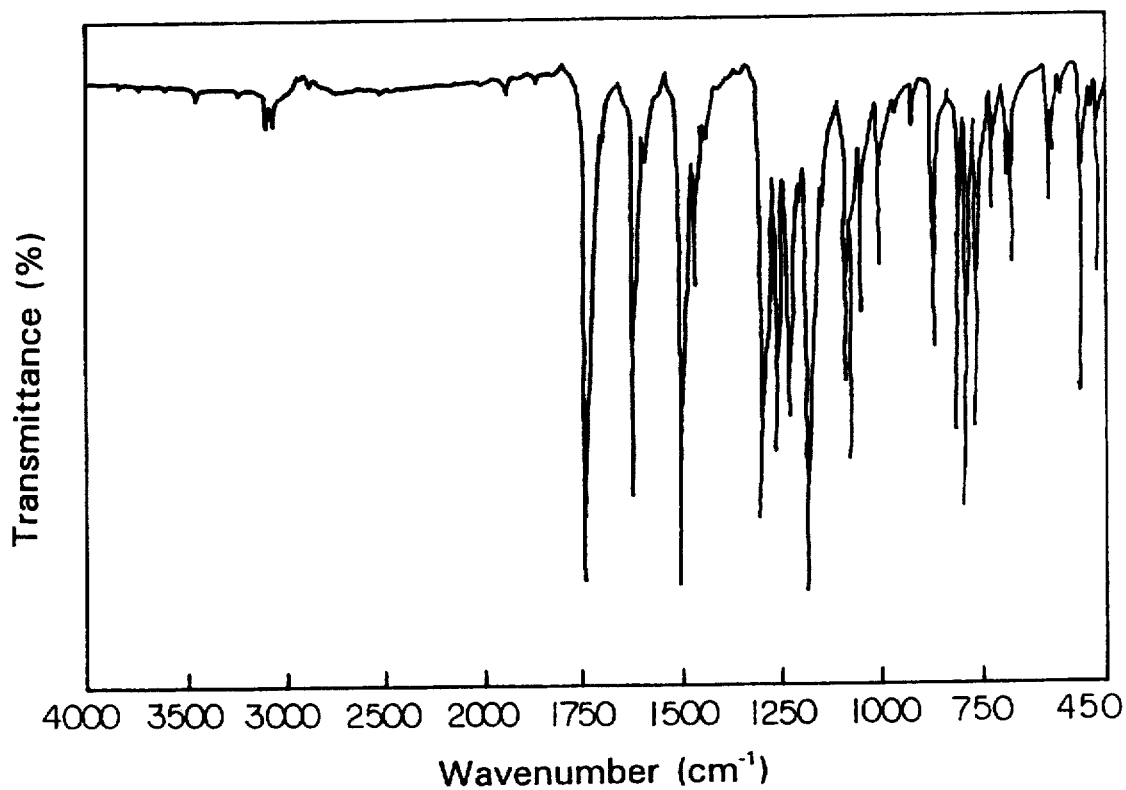

The ester had a melting point of 60.0° C. and an infrared absorption spectrum as shown in FIG. 3.

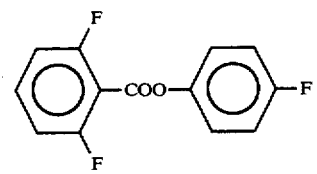

EXAMPLE 4

12 g of 2,6-dichlorobenzoic acid-(4-fluorophenyl) ester represented by the following formula was prepared similar to Example 1, except that 19.5 g of 2,6-dichlorobenzoic acid was used instead of 12.2 g of benzoic acid.

Figure 4:
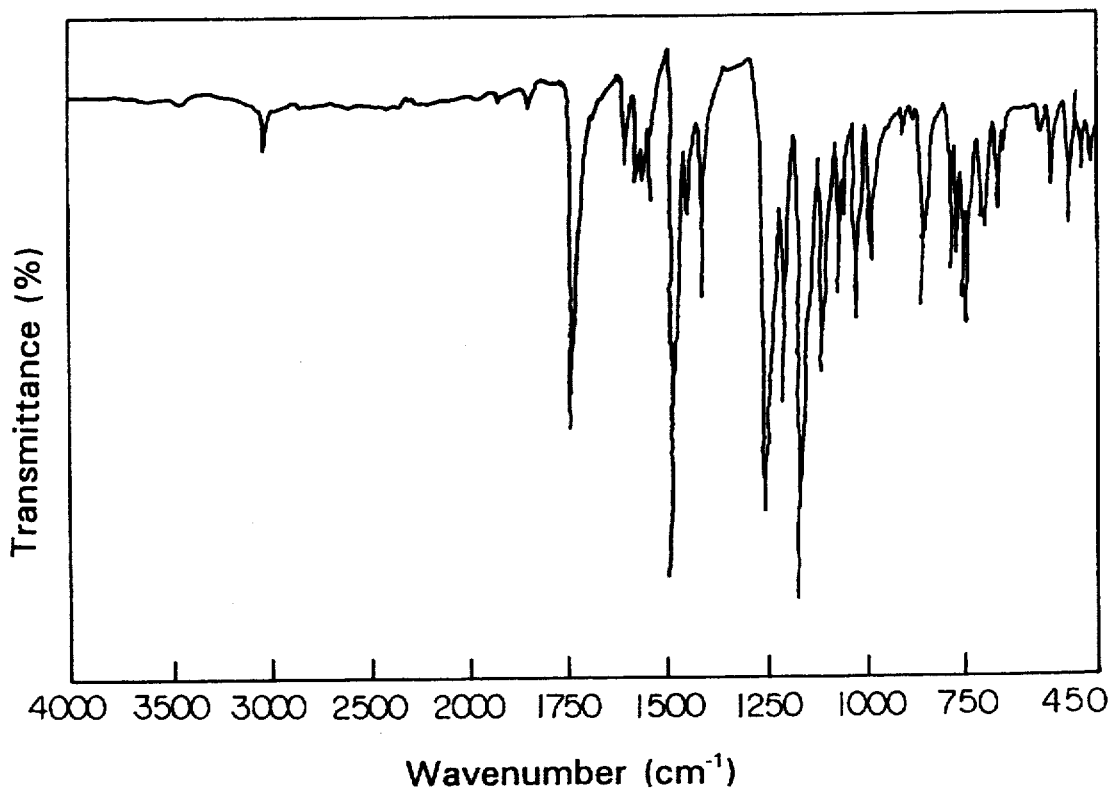

The ester had a melting point of 86.0° C. and an infrared absorption spectrum as shown in FIG. 4.

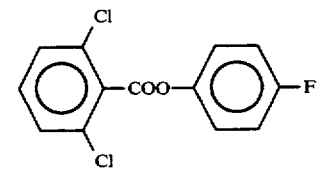

EXAMPLE 5

9 g of benzoic acid-(3,4-difluorophenyl) ester represented by the following formula was prepared similar to Example 1, except that 9.5 g of 3,4-difluorophenol was used instead of 8 g of 4-fluorophenol.

Figure 5:
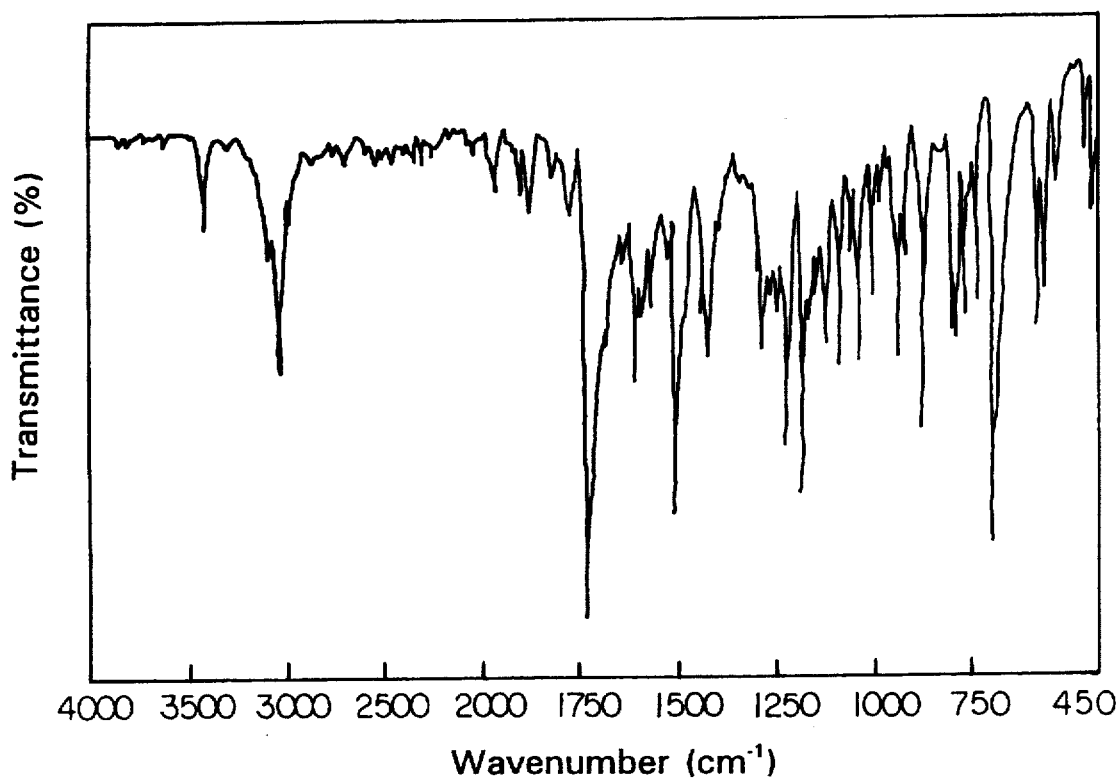

The ester had a melting point of 74.0° C. and an infrared absorption spectrum as shown in FIG. 5.

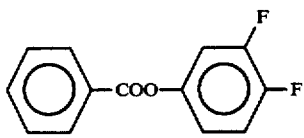

EXAMPLE 6

10 g of 2-fluorobenzoic acid-(3,4-difluoropheyl) ester represented by the following formula was prepared similar to Example 1, except that 14.6 g of 2-fluorobenzoic acid and 9.5 g of 3,4-difluorophenol were used instead of 12.2 g of benzoic acid and 8 g of 4-fluorophenol, respectively.

Figure 6:
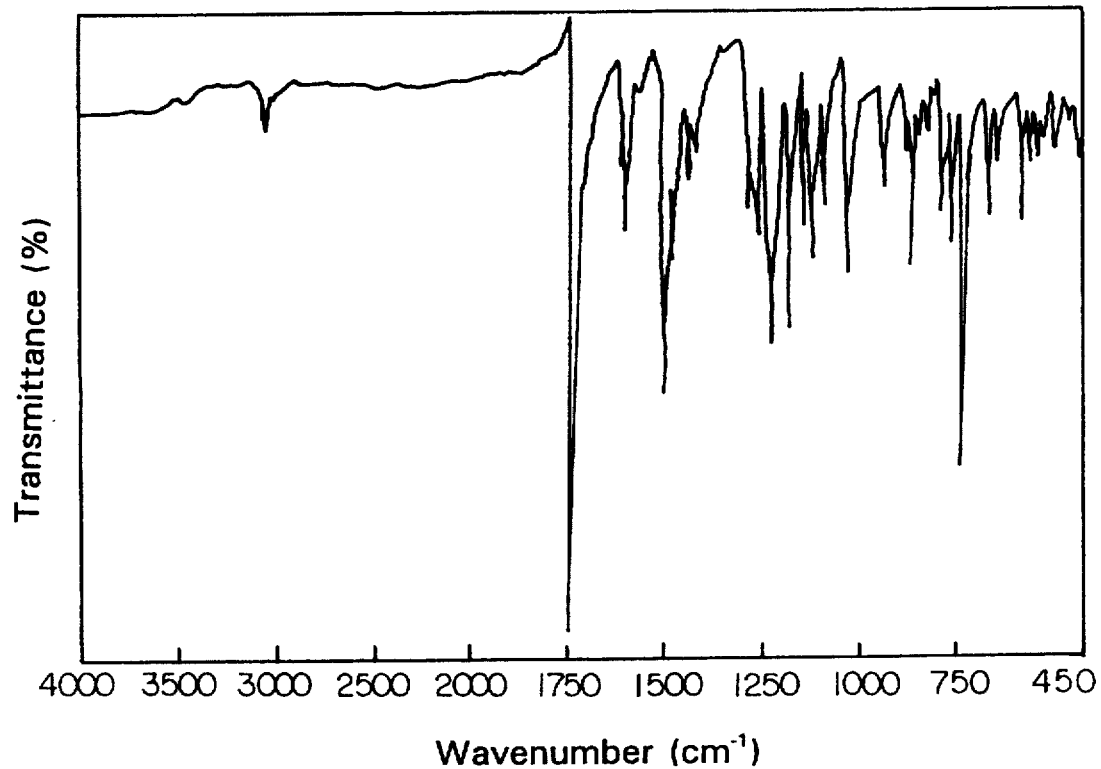

The ester had a melting point of 65.1° C. and an infrared absorption spectrum as shown in FIG. 6.

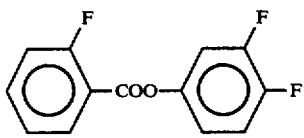

EXAMPLE 7

11 g of 2,6-difluorobenzoic acid-(3,4-difluorophenyl) ester represented by the following formula was prepared similar to Example 1, except that 16.2 g of 2,6-difluorobenzoic acid and 9.5 g of 3,4-difluorophenol were used instead of 12.2 g of benzoic acid and 8 g of 4-fluorophenol, respectively.

Figure 7:
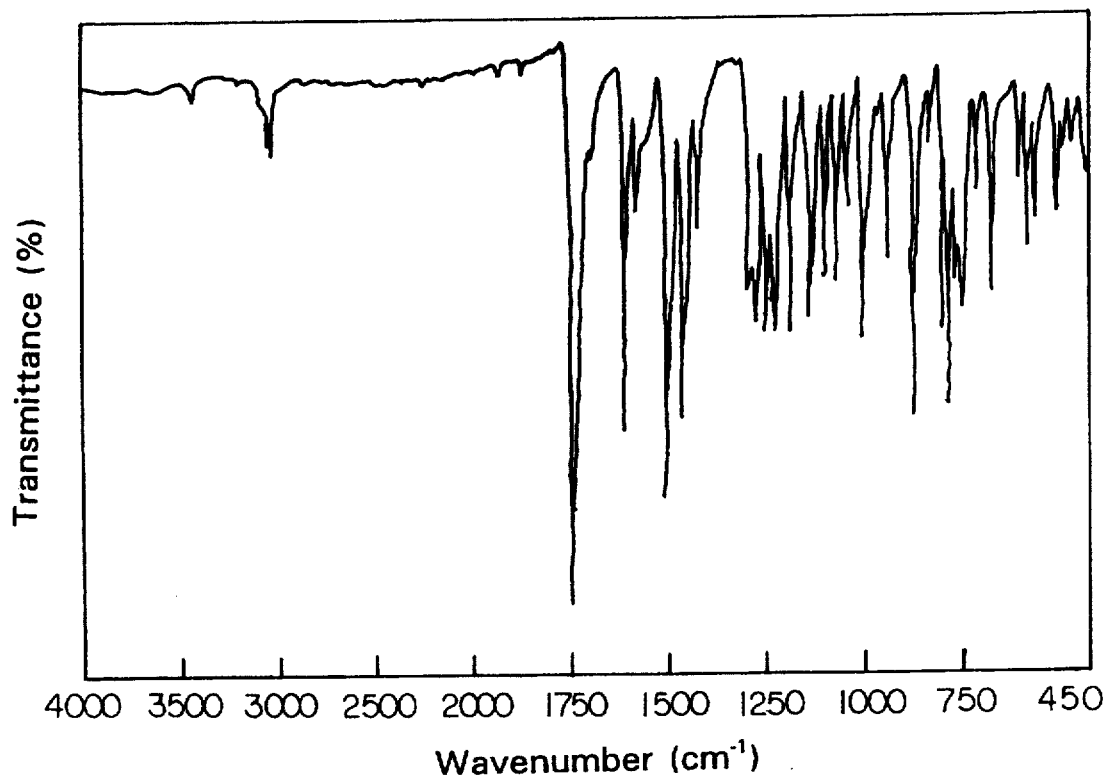

The ester had a melting point of 78.0° C. and an infrared absorption spectrum as shown in FIG. 7.

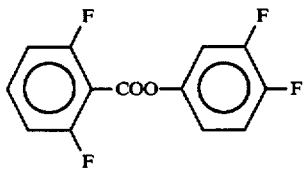

EXAMPLE 8

12 g of 2,6-dichlorobenzoic acid-(3,4-difluorophenyl) ester represented by the following formula was prepared similar to Example 1, except that 19.5 g of 2,6-dichlorobenzoic acid and 9.5 g of 3,4-difluorophenol were used instead of 12.2 g of benzoic acid and 8 g of 4-fluorophenol, respectively.

Figure 8:
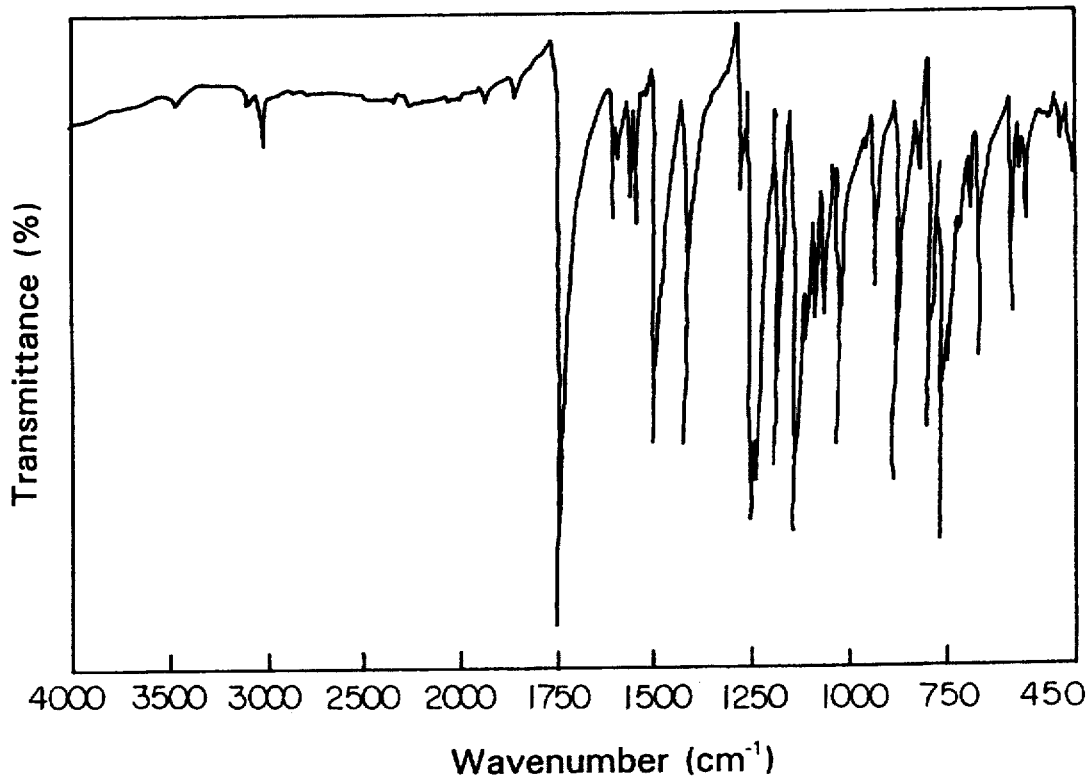

The ester had a melting point of 86.0° C. and an infrared absorption spectrum as shown in FIG. 8.

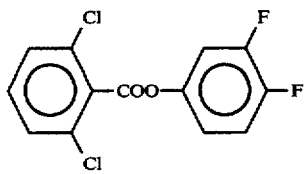

EXAMPLE 9

11 g of 2-fluorobenzoic acid-(2,3,4,-trifluorophenyl) ester represented by the following formula was prepared similar to Example 1, except that 14.6 g of 2-fluorobenzoic acid and 10.5 g of 2,3,4-trifluorophenol were used instead of 12.2 g of benzoic acid and 8 g of 4-fluorophenol, respectively.

Figure 9:
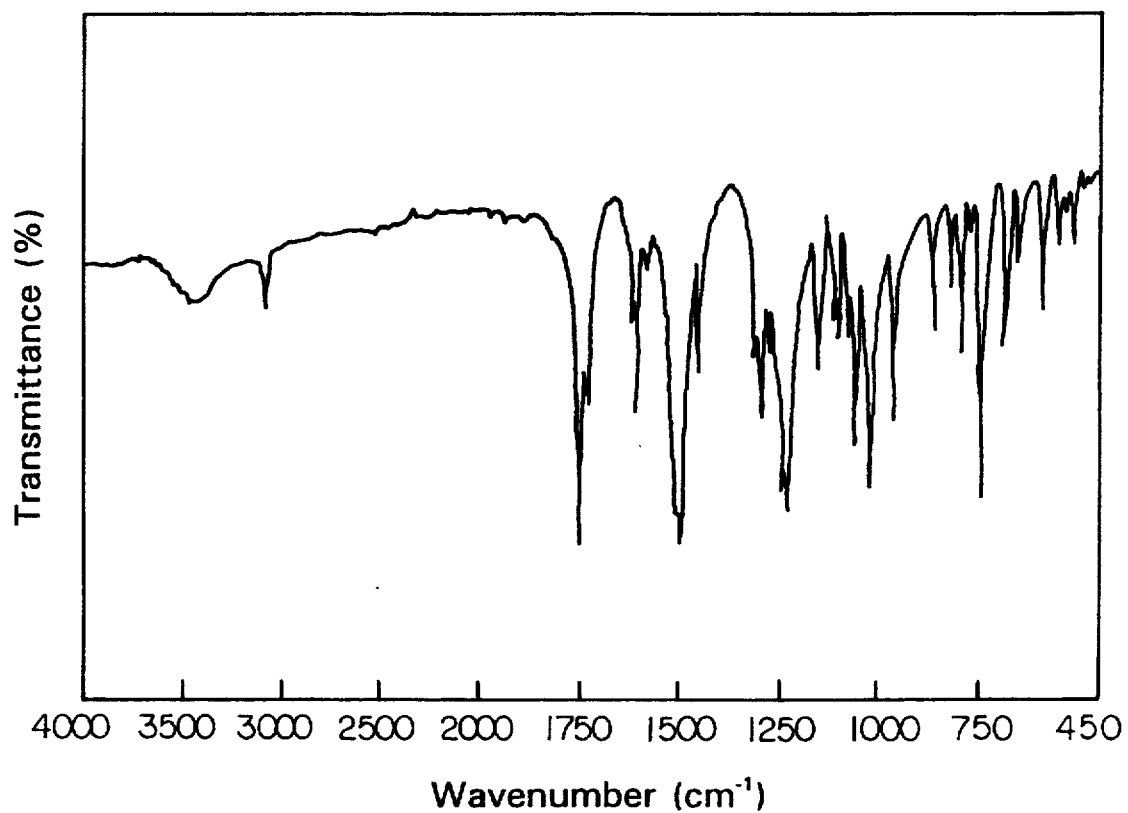

The ester had a melting point of 50.3° C. and an infrared absorption spectrum as shown in FIG. 9.

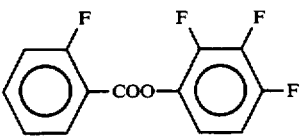

EXAMPLE 10

A liquid crystal composition was prepared by mixing with heating 10 parts by weight of the ester prepared in Example 1 with 90 parts by weight of a liquid crystal mixture composed of the following four compounds in a mixing ratio of A:B:C:D by weight of 24:36:25:15.

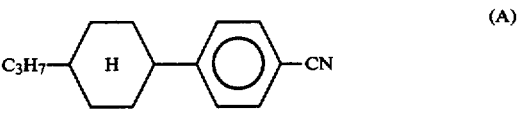

(A)

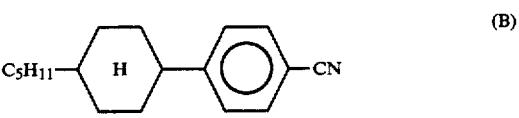

(B)

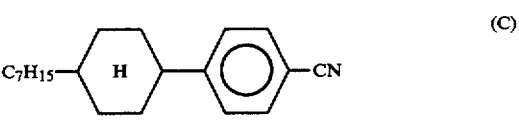

(C)

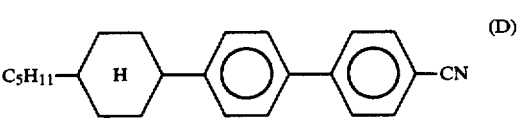

(D)

Properties of the liquid crystal composition were measured and shown in Table 1. In the table, the threshold voltage Vth was measured by loading the liquid crystal composition in a TN type liquid crystal display having a cell thickness of 9 um. The above liquid crystal mixture composed of the four compounds A, B, C, D alone had a N-I point of 72 C, a n of 0.138, a viscosity of 27.9 cp and a Vth of 1.68 V.

EXAMPLES 11–16

Liquid crystal compositions were prepared by mixing 10 parts by weight of the ester prepared in Example 2, 3, 5, 6, 7 or 9 with 90 parts by weight of the same liquid crystal mixture used in Example 10, and their properties were measured and shown in Table 1.

As can be seen from Table 1, by blending the ester derivative of the invention, The n of a conventional liquid crystal composition can be optimized, and the threshold voltage Vth can be lowered.

In most cases, the viscosity can be reduced.

TABLE 1

| Ex. No. | Compound | N-I Point (°C.) | Δn (25° C.) | Viscosity (20° C.) (cps) | Vth (25° C.) (v) |
| --- | --- | --- | --- | --- | --- |
| 10 | ⌬—COO—⌬—F | 57.0 | 0.129 | 24.9 | 1.39 |
| 11 | F-substituted ester | 59.8 | 0.130 | 25.9 | 1.39 |
| 12 | di-F-substituted ester | 61.2 | 0.129 | 25.6 | 1.37 |
| 13 | F-substituted ester | 58.5 | 0.128 | 25.7 | 1.31 |
| 14 | di-F-substituted ester | 60.5 | 0.129 | 26.3 | 1.30 |
| 15 | tri-F-substituted ester | 62.3 | 0.129 | 25.9 | 1.28 |
| 16 | tri-F-substituted ester | 56.7 | 0.127 | 28.6 | 1.29 |

We claim:

1. A liquid crystal composition consisting essentially of an ester derivative which does not exhibit liquid crystal properties and is represented by the following formula (I), and at least one liquid crystal compound $$\text{(I)}$$

wherein V, W, X, Y and Z represent a hydrogen atom or a halogen atom, respectively.

2. The liquid crystal composition of claim 1 wherein the liquid crystal compound is a member selected from the group consisting of ester compounds, cyclohexyl phenyl compounds, biphenyl compounds, pyrimidine compounds, dioxane compounds and tolan (diphenylancetylene) compounds, capable of exhibiting liquid crystallizability.

3. The liquid crystal composition of claim 1 wherein the liquid crystal compound is a member selected from the group consisting of ester compounds and cyclohexylphenyl compounds, capable of exhibiting liquid crystallizability.

4. The liquid crystal composition of claim 1, wherein X is a halogen atom.

5. The liquid crystal composition of claim 1, wherein at least one of V and W is a halogen atom.

6. The liquid crystal composition of claim 1, wherein the ester derivative has a formula of

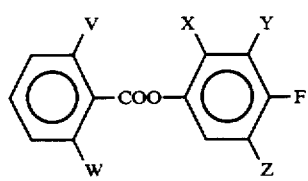 or

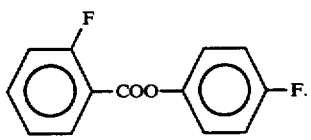

7. The liquid crystal composition of claim 4, wherein the ester derivative has a formula of

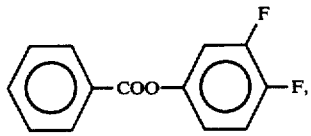

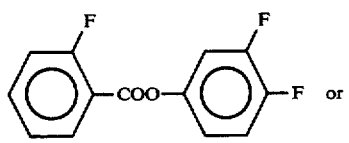

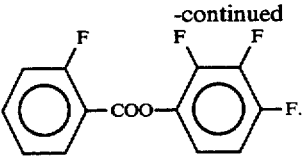

8. The liquid crystal composition of claim 1, wherein the liquid crystal compound is one or more members selected from the group consisting of 4-alkylcyclohexane carboxylic acid-(4-cyanophenyl) ester, 4-alkylcyclohexane carboxylic acid-(4-alkoxyphenyl) ester, and 4-alkyl-(4-cyanophenyl) cyclohexane.

9. The liquid crystal composition of claim 4, wherein the liquid crystal compound is one or more members selected from the group consisting of 4-alkylcyclohexane carboxylic acid-(4-cyanophenyl) ester, 4-alkylcyclohexane carboxylic acid-(4-alkoxyphenyl) ester, and 4-alkyl-(4-cyanophenyl) cyclohexane.

10. The liquid crystal composition of claim 1, wherein the ester derivative is 0.1 to 20 wt. % of the composition.

11. The liquid crystal composition of claim 4, wherein the ester derivative is 0.1 to 20 wt. % of the composition.

* * * * *

UNITED STATES PATENT AND TRADEMARK OFFICE
CERTIFICATE OF CORRECTION

PATENT NO. : 5,364,558
DATED : November 15, 1994
INVENTOR(S) : Yumiko SAKAMAKI, et al It is certified that error appears in the above-indentified patent and that said Letters Patent is hereby corrected as shown below:

Column 9, line 10; change "4" to ---1---.

Signed and Sealed this

Fourteenth Day of March, 1995

Attest:

BRUCE LEHMAN

Attesting Officer      Commissioner of Patents and Trademarks